US010792013B2

(12) United States Patent
Jensen et al.

(10) Patent No.: US 10,792,013 B2
(45) Date of Patent: Oct. 6, 2020

(54) THREE DIMENSIONAL (3D) VECTOR FLOW IMAGING WITH BIPLANE PHASED ARRAY TRANSDUCER (71) Applicant: B-K Medical Aps, Herlev (DK)

(72) Inventors: Henrik Jensen, Bagsvaerd (DK); Svetoslav Ivanov Nikolov, Farum (DK); Bo Hansen, Copenhagen (DK)

(73) Assignee: B-K Medical ApS, Herlev (DK)

( * ) Notice: Subject to any disclaimer, the term of this patent is extended or adjusted under 35 U.S.C. 154(b) by 1184 days.

(21) Appl. No.: 14/893,569

(22) PCT Filed: May 29, 2013

(86) PCT No.: PCT/IB2013/001087
§ 371 (c)(1),
(2) Date: Nov. 24, 2015

(87) PCT Pub. No.: WO2014/191784
PCT Pub. Date: Dec. 4, 2014

(65) Prior Publication Data
US 2016/0106391 A1 Apr. 21, 2016

(51) Int. Cl.
A61B 8/00 (2006.01)
A61B 8/06 (2006.01)
(Continued)

(52) U.S. Cl.
CPC .............. A61B 8/4488 (2013.01); A61B 8/06 (2013.01); A61B 8/145 (2013.01); A61B 8/4494 (2013.01);
(Continued)

(58) Field of Classification Search
None
See application file for complete search history.

(56) References Cited

U.S. PATENT DOCUMENTS 4,671,293 A * 6/1987 Shaulov .............. B06B 1/0629
600/447
6,186,950 B1 * 2/2001 Averkiou ................ A61B 8/06
600/440
(Continued)

FOREIGN PATENT DOCUMENTS

JP H03-202052 A 9/1991
WO 2001089397 A1 11/2001

OTHER PUBLICATIONS

International Search Report for PCT/IB2013/001087, dated Feb. 3, 2014.

Primary Examiner — Katherine L Fernandez
(74) Attorney, Agent, or Firm — Anthony M. Del Zoppo, III; Daugherty & Del Zoppo Co., LPA (57) ABSTRACT An ultrasound imaging system (100) includes a transducer array (102). The transducer array includes a first set of transducer elements (206 or 208, 302 or 304) and a second set of transducer elements (208 or 206, 304 or 302). The first and second sets of transducer elements includes long axes and are angularly offset from each other by a non-zero angle with respect to the long axes. The ultrasound imaging system further includes a velocity processor (120) that processes echoes received by the first and second sets of transducer elements and determines an axial and two transverse flow velocity components based on the received echoes.

24 Claims, 4 Drawing Sheets (51) Int. Cl.
*A61B 8/14* (2006.01)
*G01S 15/89* (2006.01)
*A61B 8/08* (2006.01)

(52) U.S. Cl.
CPC .......... *A61B 8/5207* (2013.01); *A61B 8/5223* (2013.01); *A61B 8/54* (2013.01); *A61B 8/56* (2013.01); *G01S 15/8925* (2013.01); *G01S 15/8929* (2013.01); *G01S 15/8984* (2013.01)

(56) References Cited

U.S. PATENT DOCUMENTS

| | | | |
|---|---|---|---|
| 6,419,633 B1 | 7/2002 | Robinson | |
| 7,497,828 B1 * | 3/2009 | Wilk | A61B 5/6804 |
| | | | 600/443 |
| 2003/0100832 A1 * | 5/2003 | Criton | A61B 8/06 |
| | | | 600/443 |
| 2003/0107303 A1 * | 6/2003 | Mohr, III | B06B 1/064 |
| | | | 310/365 |
| 2013/0069484 A1 * | 3/2013 | Hynynen | B06B 1/0622 |
| | | | 310/334 |
| 2014/0269206 A1 * | 9/2014 | Mo | A61B 8/56 |
| | | | 367/138 |

* cited by examiner

THREE DIMENSIONAL (3D) VECTOR FLOW IMAGING WITH BIPLANE PHASED ARRAY TRANSDUCER

RELATED APPLICATION

This application is a national filing of PCT application Serial No. PCT/IB2013/001087, filed May 29, 2013, published as WO2014/191784 on Dec. 4, 2014. This application claims priority to PCT application Serial No. PCT/IB2013/001087, published as WO2014/191784 on Dec. 4, 2014.

TECHNICAL FIELD

The following generally relates to ultrasound imaging and more particularly to three dimensional (3D) vector flow imaging with a biplane phased array transducer, and is described with particular application to an ultrasound system.

BACKGROUND

Ultrasound imaging has been used to determine information about the interior characteristics of an object or a subject. This has included producing one or more images of an interior structure such as a tubular or other structure and an estimation of flow velocity of structure flowing in a cavity of the tubular structure, which has been visually displayed in connection with the image.

Expired patent U.S. Pat. No. 4,671,293 shows a phased array transducer that includes a slice of a composite piezoelectric material with an array of transducer elements disposed on each side of the material, orthogonal to each other. The electrical connections to the arrays are shared and switched such that the elements on one side are grounded while the elements on the other side are employed, and vice versa. An image, which does not include any flow information, is generated for each of the planes, and a clinician has had to view the two images and mentally construct the 3D landscape of the scanned object.

For flow velocity estimation, in one instance, a pulse-echo field oscillates in the axial direction along the axis of the ultrasound beam and only the axial velocity component along the z-axis or depth is estimated; the transverse velocity components cannot be estimated. Generally, scatterers traversing the ultrasound beam will produce a signal with a frequency component proportional to the axial velocity. The basic mechanism that allows this estimation is the oscillations in the transmitted pulse.

A two-dimensional (2D) transverse oscillation (TO) velocity estimation approach has been used to estimate the axial component and one of the transverse velocity components (elevation or azimuth). For this approach, using the same basic mechanism noted above, a transverse oscillation is introduced in the ultrasound field, and this oscillation generates received signals that depend on the transverse oscillation.

The basic idea is to create a double-oscillating pulse-echo field using a one dimensional (1D) transducer array. This can be been done by using the same transmit beam as used in conventional flow velocity estimation and predetermined apodization profiles in receive. This TO approach is discussed in Udesen, "Investigation of Transverse Oscillation Method," IEEE Trans. Ultrason., Ferroelec., Freq. Contr., vol. 53, pp. 959-971, 2006.

A three-dimensional (3D) transverse oscillation (TO) velocity estimation approach has been used to estimate velocity components in all three directions, including the axial component and one or both of the transverse velocity components. This approach is described in international (PCT) patent application serial number PCT/IB2011/002383, filed Oct. 11, 2011, and entitled "Three Dimensional (3D) Transverse Oscillation Vector Velocity Ultrasound Imaging."

For this approach, a matrix or two-dimensional (2D) transducer array of transducer elements (e.g., 32×32, 64×64, etc.) is used. However, a 2D transducer array, such as the 2D transducer array described in PCT/IB2011/002383, requires a channel for each of the individual transducer elements of the transducer array. Thus, a 32×32 transducer array would have 1024 channels, a 96×96 transducer array would have 9216 channels, etc.

SUMMARY

Aspects of the application address the above matters, and others.

In one aspect, an ultrasound imaging system includes a transducer array. The transducer array includes a first set of transducer elements and a second set of transducer elements. The first and second sets of transducer elements includes long axes and are angularly offset from each other by a non-zero angle with respect to the long axes. The ultrasound imaging system further includes a velocity processor that processes echoes received by the first and second sets of transducer elements and determines an axial and two transverse flow velocity components based on the received echoes.

In another aspect, a method includes receiving first echoes in response a first ultrasound beam traversing a first plane in a first direction. The method further includes receiving second echoes in response a second ultrasound beam traversing a second plane in a second direction. The first and second directions are at an angle with respect to each other. The method further includes estimating three orthogonal flow velocity components based on the first and second echoes.

In another aspect, a computer readable storage medium is encoded with computer readable instructions, which, when executed by a processor, cause the processor to: process data generated by a biplane transducer array utilized in a phased array mode and determine 3D orthogonal velocity components based on the data and with a 3D vector flow imaging processing algorithm.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which.

DETAILED DESCRIPTION

The following general describes a 3D vector flow imaging approach employing a biplane transducer array (included in a single transducer or two separate transducers) in a phased array manner and processing the received echoes utilizing a 3D transverse oscillation (TO) velocity estimation. The biplane array can be controlled such that one of the arrays is at electrical ground and the other transmits and/or receives, or that the arrays concurrently transmit and/or receive, but are electrically driven differentially.

Figure 1:
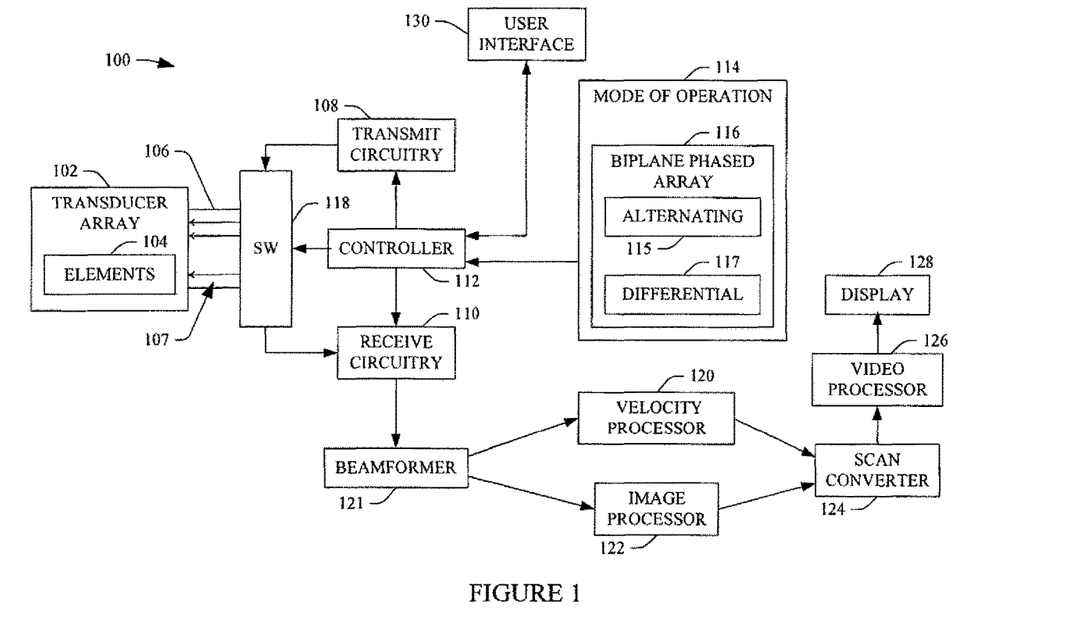
FIG. 1 schematically illustrates an ultrasound imaging system including a biplane transducer array and a velocity processor that estimates 3D vector flow velocity components.

Initially referring to FIG. 1, an example ultrasound imaging system 100 is illustrated.

The ultrasound imaging system 100 includes a transducer array 102 with a plurality of transducer elements 104. The transducer array 102 can be linear, curved, and/or otherwise shaped, fully populated or sparse and/or a combination hereof, etc. The transducer array 102 includes a single biplane array, in which each of the arrays can be utilized in a phased array manner. However, other configurations, including separate transducer arrays, are also contemplated and discussed herein.

Figure 2:
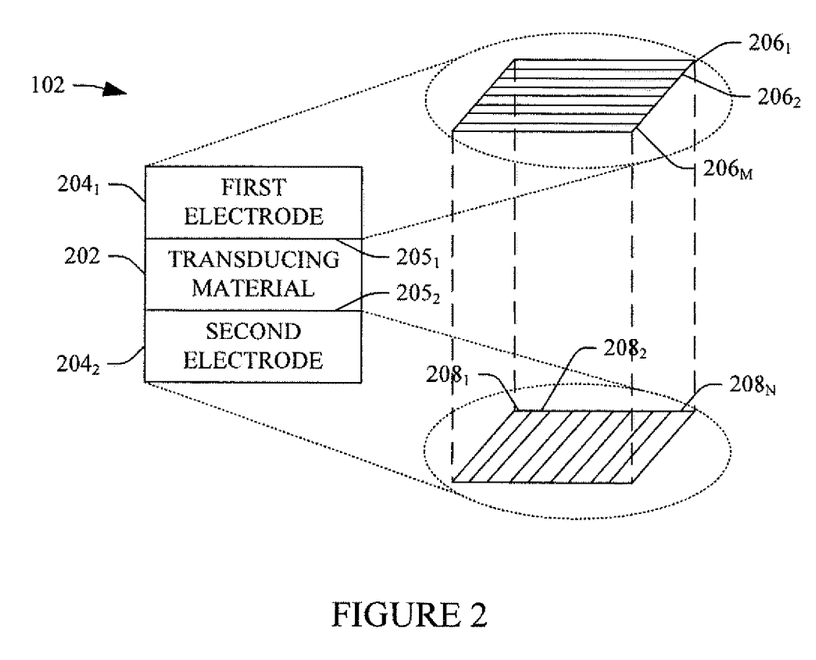
FIG. 2 schematically illustrates an example of the biplane transducer array of FIG. 1 in which the biplane transducer array includes a single biplane transducer that can be employed in a phased array manner.

Briefly turning to FIG. 2, an example of the single biplane array transducer 102 is illustrated. The single biplane array transducer 102 includes a transducing material 202 (e.g., piezoelectric, etc.) sandwiched between a first electrode $204_1$ and a second electrode $204_2$ (collectively referred to as electrodes 204). The first and second electrodes 204 are affixed to first and second opposing major surfaces $205_1$ and $205_2$ of material 202.

In the illustrated embodiment, the first electrode $204_1$ includes M transducer elements $206_1$, $206_2$, . . . , $206_M$ (collectively referred to as transducer elements 206), each extending across a face of the transducing material in a first direction and arranged, with respect to each other, generally parallel in a second direction, which is orthogonal to the first direction. The transducer elements 206 can be created by scoring, dicing, etc. surface of the electrode $204_1$.

In the illustrated embodiment, the second electrode $204_2$ includes N transducer elements $208_1$, $208_2$, . . . , $208_N$ (collectively referred to as transducer elements 208), each extending across a face of the transducing material in a first direction and arranged, with respect to each other, generally parallel in a second direction, which is orthogonal to the first direction. The transducer elements 208 can be created by scoring, dicing, etc. surface of the electrode $204_2$.

The transducer elements 206 and the transducer elements 208 include long axes and are spatially arranged with respect to each other at an angle with respect to the long axes. For example, in the illustrated embodiment, the transducer elements 206 and 208 are arranged approximately orthogonal to each other, forming rows and columns of transducer elements. In another example, the transducer elements 206 and 208 are arranged at one or more other angels with respect to each other.

In the illustrated example, the transducer elements 206 can be considered rows or columns, with the transducer elements 208 considered columns or rows. Example configurations of the transducer elements 206 and 208 include, but are not limited to, 16 rows by 16 columns, 32 rows by 32 columns, 64 rows by 64 columns, 96 rows by 96 columns, etc. Other configurations include rectangular configurations in which M≠N. Non-square and non-rectangular configurations are also contemplated herein.

Returning to FIG. 1, a communications path 106 includes individual channels 107 for each of the individual columns and rows of transducer elements 206 and 208. Each channel allows each row and each column to be individually controlled for excitation and/or reception. This includes simultaneous or individual steering, focusing and apodization of the transducer elements 206 and 208.

As such, with 96 rows and 96 columns, up to 192 (96+96) elements can be concurrently or individually controlled. Such control, which, in one instance, may provide for a performance comparable to 96×96 matrix or 2D array. However, only 192 are used instead of the 9216 channels required for the 96×96 matrix or 2D array.

Transmit circuitry 108 generates a set of pulses that are conveyed to the transducer elements 104. The set of pulses excites a corresponding group of the transducer elements 104, causing the transducer elements 104 to transmit ultrasound signals into an examination or scan field of view. In the illustrated embodiment, the transmit circuitry 108 can be controlled to generate a set of pulses that excite the transducer elements 104 in accordance with a phased array approach.

Receive circuitry 110 receives echoes generated in response to the transmitted ultrasound signals. The echoes, generally, are a result of the interaction between the emitted ultrasound signals and the structure (e.g., organ cells, flowing blood cells, etc.) in the scan field of view. In the illustrated embodiment, the receive circuitry 110 receives echoes generated in response to the set of pulses produced by at least a phased array.

A controller 112 controls one or more of the transmit circuitry 108 or receive circuitry 110. Such control can be based on available modes of operation 114, including a biplane phased array 116 mode such as an alternating mode of operation 115, a differential mode of operation 117 and/or other mode of operation. The controller 112 also controls a switch (SW) 118, which switches between the transmit circuitry 108 and the receive circuitry 110 for excite and receive operations.

With the alternating mode of operation 115, such control includes exciting the transducer elements 104 of one of the electrodes 204 and electrically grounding the transducer elements 104 of the other of the electrodes 204, and then alternating which electrode 204 is active and which is grounded. Grounding can be achieved through active clamping of transmitters and/or otherwise.

With the differential mode of operation 117, such control includes exciting the transducer elements 104 of both electrodes 204 simultaneously such that the transducer elements 104 are used for transmit and/or receive, simultaneously. For instance, the first electrode $204_1$ can be excited with one polarity to control steering, focusing and apodization in one direction, and the second electrode $204_2$ can be excited with the opposite polarity to control steering, focusing, and apodization in the other direction.

In one instance, with the differential mode of operation 117, the electrodes 204 are excited such that more than half of the transducer elements are excited for transmit and receive, simultaneously. It is to be appreciated that this may allow for increasing the amount of information available, which may further improve the estimation of the 3D flow vector velocity.

A beamformer 121 processes the received echoes and produces data for determining the 3D flow velocity components and for generating images in A-mode, B-mode, and/or other modes. The beamformer 121 may be a single beamformer (as shown) or include a plurality of sub-beamformers. Alternatively, a plurality of individual beamformers may be utilized.

A velocity processor 120 processes the beamformed data. Such processing includes determining one or more of the 3D velocity components, including an axial velocity component and a transverse component such as an elevation velocity component and/or an azimuth velocity component. A suitable approach to beamforming the echoes and determining the 3D flow velocity components is described in international (PCT) patent application serial number PCT/IB2011/002383, filed Oct. 11, 2011, and entitled "Three Dimensional (3D) Transverse Oscillation Vector Velocity Ultrasound Imaging," which is incorporated herein by reference.

An image processor 122 also processes the beamformed data. For B-mode, the image processor 122 processes the data and generates a sequence of focused, coherent echo samples along focused scanlines of a scanplane. The image processor 122 may also be configured to process the scanlines to lower speckle and/or improve specular reflector delineation via spatial compounding and/or perform other processing such as FIR filtering, IIR filtering, etc.

A scan converter 124 scan converts the output of the velocity processor 120 and the image processor 122 and generates data for display, for example, by converting the data to the coordinate system of the display.

A video processor 126 visually presents one or more images and/or flow velocity information via a display monitor 128. Such presentation can be in an interactive graphical user interface (GUI), which allows the user to selectively rotate, scale, and/or manipulate the displayed data, via a mouse, a keyboard, a touch-screen, etc.

A user interface (UI) 130 provides an interface for interacting with the system 100. Such interaction may include user interacting for selecting a mode of operation, etc. The US 130 may include one or more input devices (e.g., a button, a knob, a slider, a touch pad, etc.) and/or one or more output devices (e.g., a display screen, lights, a speaker, etc.).

One or more of the components of the system 100 may be implemented via a processor (i.e., a microprocessor, cpu, and/or the like) executing computer readable instructions stored on computer readable storage medium (which does not include transitory medium) such as a physical memory device. Additionally or alternatively, a component can be implemented via an instruction encoded in transitory medium.

Figure 3:
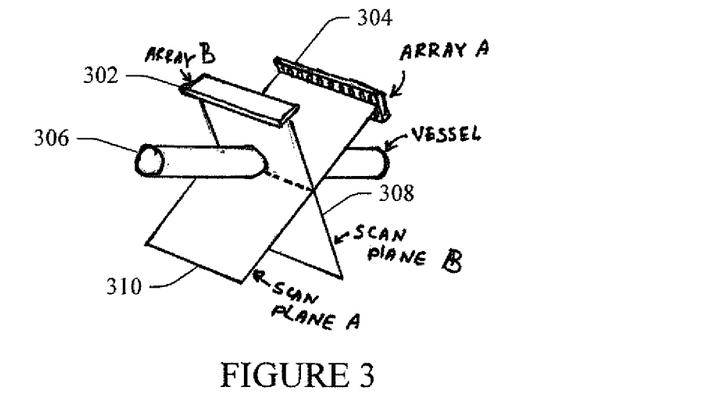
FIG. 3 schematically illustrates a perspective view of a variation of FIG. 2 in which the transducer array includes two separate transducer arrays to produce intersecting beams.
Figure 4:
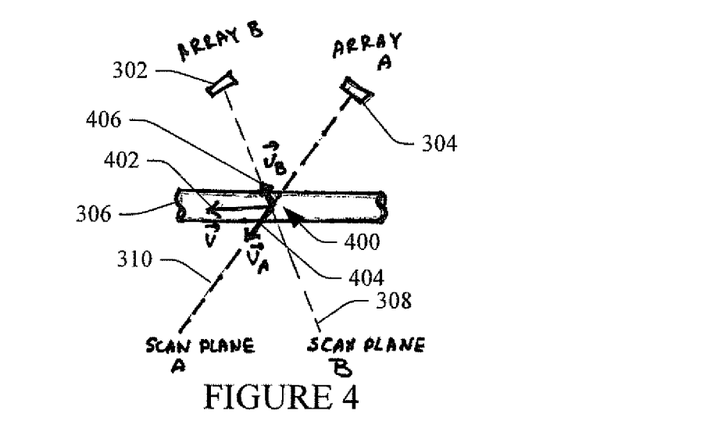
FIG. 4 schematically illustrates a side view of the variation in FIG. 3, showing the flow velocity components along a vessel long axis and along the two planes of the two beams.
Figure 5:
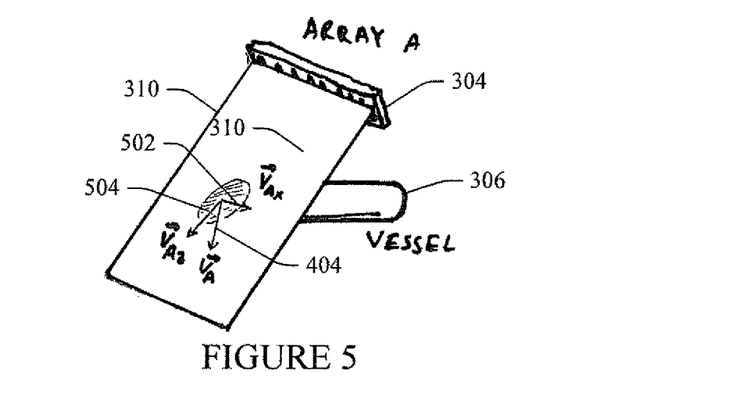
FIG. 5 schematically illustrates a perspective view of the variation in FIG. 2, showing the flow velocity components along one of the two planes.

In FIGS. 1 and 2, the transducer array 102 includes a single biplane phased array. FIGS. 3, 4 and 5 illustrate a variation in which the transducer array 102 includes two separate transducer arrays.

More specifically, FIG. 3 schematically illustrates a perspective view of a variation of FIG. 2 in which the transducer array includes two separate transducer arrays to produce two intersecting beams. FIG. 4 schematically illustrates a side view of the variation of FIG. 2, showing the flow velocity components along the vessel long axis and along the two planes of the two beams.

FIG. 5 schematically illustrates a perspective view of the variation of FIG. 2, showing the flow velocity components along one of the two planes. In FIGS. 3, 4 and 5, the transducer array 102 includes a first transducer array 302 and a second transducer array 304. The first and second transducer arrays 302 and 304 are side by side and angularly offset from each other by a predetermined known angle.

The first and second transducer arrays 302 and 304 are shown in connection with a tubular structure 306. In the illustrated embodiment, the tubular structure 306 is a vessel. However, in another instance, the tubular structure 306 is another tubular structure. A first scan plan 308 corresponds to the first transducer array 302, and a second scan plan 310 corresponds to the second transducer array 304. The scan planes 308 and 310 are angularly offset from each other by the predetermined known angle.

The first and second scan planes 308 and 310 intersect at a region 400 in the tubular structure 306. The 3D transverse flow 402 can be expressed through: $\vec{V}=\vec{V}_A+\vec{V}_B$, where $V_A$ 404 is the velocity in the second plane 310 and $V_B$ 406 is the velocity in the first plane 308. $V_A$ 404 can be determined from $\vec{V}_A=\vec{V}_{AX}+\vec{V}_{AZ}$, where $\vec{V}_{AX}$ 502 and $\vec{V}_{AZ}$ 504 are the axial and transverse components, and $V_B$ 406 can be determined from $\vec{V}_B=\vec{V}_{BX}+\vec{V}_{BZ}$ where $\vec{V}_{BX}$ and $\vec{V}_{BZ}$ are the axial and transverse components.

Both $V_A$ 404 and $V_B$ 406 can be determined using a transverse oscillation approach and/or other approach. This includes the transverse oscillation approach(s) discussed herein and/or other transverse oscillation approaches.

In another variation, the transducer array 102 includes a 1.5D array, and the 1.5D array transducer is used to acquire data that can be employed to estimate the 3D vector flow information. In one instance, the 1.5D array transducer includes three rows, and the outer rows are electrically coupled in parallel to acquire such data. With this approach, at least a portion of the field in the center is modulated similar as to when transverse oscillations are used to estimate 2D vector flow.

Figure 6:
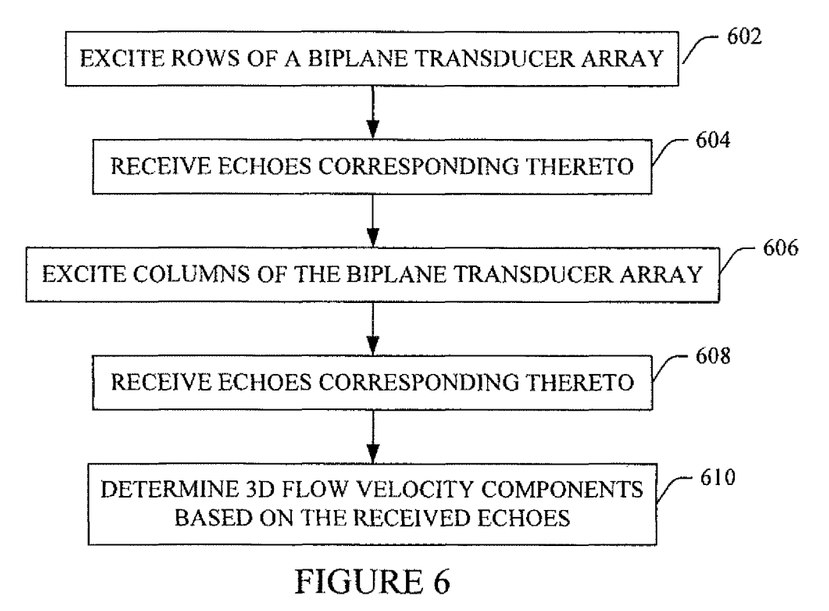
FIG. 6 illustrates a method in accordance with the example discussed in connection with FIGS. 1 and 2.
Figure 7:
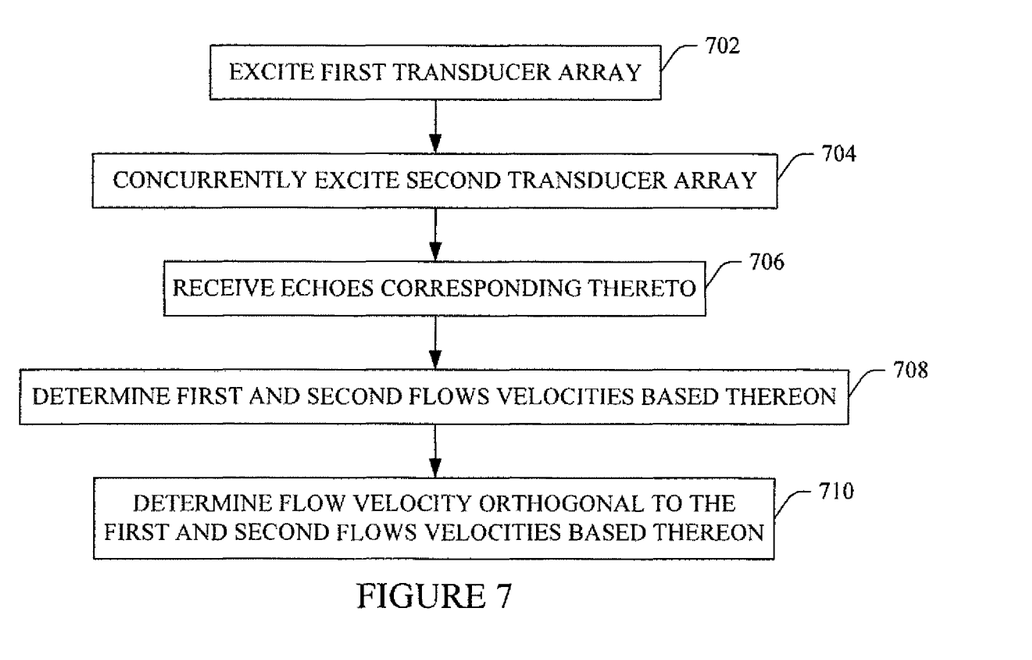
FIG. 7 illustrates a method in accordance with the example discussed in connection with FIGS. 3, 4 and 5.

FIGS. 6 and 7 illustrate example methods.

FIG. 6 illustrates a method in accordance with the examples of FIGS. 1 and 2.

It is to be understood that the following acts are provided for explanatory purposes and are not limiting. As such, one or more of the acts may be omitted, one or more acts may be added, one or more acts may occur in a different order (including simultaneously with another act), etc.

At 602, rows of transducer elements of transducer array are successively excited to transmit and steer and focus a first ultrasound beam in a first plane.

At 604, first echoes corresponding to the first plane and produced in response to the first ultrasound beam are received.

At 606, columns of transducer elements of the transducer array are successively excited to transmit and steer and focus a second ultrasound beam in a second different plane, which is at a predetermined angle (e.g., 90 degrees, etc.) with respect to the first plane.

At 608, second echoes corresponding to the second plane and produced in response to the second ultrasound beam are received.

At 610, three orthogonal flow velocity components are determined based on the first and second echoes, using a 3D TO velocity estimation and/or other approach.

FIG. 7 illustrates a method in accordance with the examples of FIGS. 1, 3, 4, and 5.

It is to be understood that the following acts are provided for explanatory purposes and are not limiting. As such, one or more of the acts may be omitted, one or more acts may be added, one or more acts may occur in a different order (including simultaneously with another act), etc.

At 702, a first transducer array of two separate transducers transmits a first beam in a first direction through an imaging field of view.

At 704, a second transducer array of the two separate transducers transmits, concurrently with the first transducer array, a second beam in a second direction through an imaging field of view, wherein the first and second directions intersect in a field of view.

At 706, first echoes corresponding to the first beam are received, and second echoes corresponding to the second beam are received.

At 708, first and second flow velocities in the first and second directions are determined.

At 710, a flow velocity orthogonal to the first and second directions and along a flow of flowing structure is determined based on the along an axis of the first and second flow velocities.

The methods described herein may be implemented via one or more processors executing one or more computer readable instructions encoded or embodied on computer readable storage medium which causes the one or more processors to carry out the various acts and/or other functions and/or acts. Additionally or alternatively, the one or more processors can execute instructions carried by transitory medium.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An ultrasound imaging system, comprising:
   a single biplane transducer array, including:
      a first electrode including a first set of transducer elements;
      a second electrode including a second set of transducer elements; and
      a single-layer piezoelectric transducing material disposed between and on the first and the second electrodes, wherein the first and the second sets of transducer elements include long axes and are angularly offset from each other by a non-zero angle with respect to the long axes;
   a controller that generates a first signal that concurrently excites both of the first and the second sets of the transducer elements, wherein the first and the second sets of transducer elements are excited with an opposite polarity; and
   a velocity processor that processes echoes received by the first and the second sets of the transducer elements and determines an axial and two transverse flow velocity components based on the received echoes.

2. The system of claim 1, wherein the first and the second sets of transducer elements are orthogonal to each other with respect to the long axes.

3. The system of claim 1, wherein the controller excites the first or the second sets of transducer elements, employing a phased array algorithm to at least one of steer or focus ultrasound beams transmitted therefrom.

4. The system of claim 1, further comprising:
   a communications path, including individual channels, each channel in electrical communication with a different group of elements of the first or the second sets of transducer elements.

5. The system of claim 1, wherein the first electrode includes a first number of the transducer elements, each extending across a first face of the piezoelectric transducing material in a first direction and arranged, with respect to each other, generally parallel in a second direction, which is orthogonal to the first direction.

6. The system of claim 5, wherein the second electrode includes a second number of the transducer elements, each extending across a second face of the piezoelectric transducing material in a third direction and arranged, with respect to each other, generally parallel in a fourth direction, which is orthogonal to the third direction.

7. The system of claim 6, wherein the non-zero angle is ninety degrees.

8. The system of claim 7, wherein the first and second sets of the transducer elements form rows and columns of transducer elements.

9. The system of claim 8, further comprising:
   a communications path, including individual channels, each channel in electrical communication with a different row or column of the first or the second sets of transducers.

10. The system of claim 6, wherein the non-zero angle is not ninety degrees.

11. The system of claim 6, wherein the first and the second number of the transducer elements is equal.

12. The system of claim 6, wherein the first and the second number of the transducer elements are not equal.

13. The system of claim 6, wherein the transducer array is a rectangular shaped transducer array.

14. The system of claim 1, wherein the controller concurrently excites both of the first and the second sets of transducer elements with the opposite polarity for a simultaneous transmit operation by both of the first and second sets of transducer elements.

15. The system of claim 1, wherein the controller concurrently excites both of the first and the second sets of transducer elements with the opposite polarity for a simultaneous receive operation by both of the first and the second sets of transducer elements.

16. The system of claim 1, wherein the controller concurrently excites both of the first and the second sets of transducer elements with the opposite polarity to control steering, focusing and apodization of one of the first and the second sets of transducer elements in one direction and steering, focusing and apodization of the other of the first and second sets of transducer elements in a different direction.

17. The system of claim 1, wherein the controller concurrently excites both of the first and the second sets of transducer elements with the opposite polarity such that more than half of the transducer elements are simultaneously excited for transmit and receive.

18. A method, comprising:
   generating, with a controller, a first signal that concurrently excites both first and second sets of transducer elements of a transducer array, wherein the first and second sets of transducer elements are first and second electrodes disposed on opposing major surfaces of a single-layer piezoelectric transducing material, wherein the first and the second electrodes sandwich the piezoelectric transducing material, include long axes and are angularly offset from each other by a non-zero angle with respect to the long axes, and the first and the second sets of transducer elements are excited with an opposite polarity; and processing, with a velocity processor, echoes received by the first and the second sets of transducer elements to determine an axial and two transverse flow velocity components based on the received echoes.

19. The method of claim 18, further comprising:
concurrently exciting both of the first and the second sets of transducer elements with the opposite polarity for a simultaneous transmit operation by both of the first and second sets of transducer elements.

20. The method of claim 19, further comprising:
concurrently exciting both of the first and the second sets of transducer elements with the opposite polarity for a simultaneous receive operation by both of the first and second sets of transducer elements.

21. The method of claim 18, further comprising:
concurrently exciting both of the first and the second sets of transducer elements with the opposite polarity for a simultaneous receive operation by both of the first and the second sets of transducer elements.

22. The method of claim 18, further comprising:
concurrently exciting both of the first and the second sets of transducer elements with the opposite polarity to control steering, focusing and apodization of one of the first and the second sets of transducer elements in one direction and steering, focusing and apodization of the other of the first and the second sets of transducer elements in a different direction.

23. The method of claim 18, further comprising:
concurrently exciting both of the first and the second sets of transducer elements with the opposite polarity such that more than half of the transducer elements are simultaneously excited for transmit and receive.

24. A non-transitory computer-readable storage medium storing instructions that when executed by a computer cause the computer to perform a method comprising:
generating a first signal that concurrently excites both first and second sets of transducer elements of a transducer array, wherein the first and the second sets of transducer elements are first and second electrodes disposed on opposing major surfaces of a single-layer piezoelectric transducing material, wherein the first and the second electrodes sandwich the piezoelectric transducing material, include long axes and are angularly offset from each other by a non-zero angle with respect to the long axes, and the first and the second sets of transducer elements are excited with an opposite polarity; and processing echoes received by the first and the second sets of transducer elements to determine an axial and two transverse flow velocity components based on the received echoes.

* * * * *